United States Patent [19]

Allen et al.

[11] Patent Number: 5,587,481
[45] Date of Patent: Dec. 24, 1996

[54] PREPARATION OF (S)-DECAHYDROISOQUINOLINE-3-CARBOXYLIC ACID T-BUTYLAMIDE

[75] Inventors: David R. Allen, Oak Brook, Ill.; Scott Jenkins, San Francisco, Calif.; Loraine Klein, Streamwood, Ill.; Robert Erickson, Des Plaines, Ill.; Diane Froen, Hoffman Estates, Ill.

[73] Assignee: The Monsanto Company, St. Louis, Mo.

[21] Appl. No.: 603,744

[22] Filed: Feb. 20, 1996

[51] Int. Cl.$^6$ .................................................. C07D 217/16
[52] U.S. Cl. .......................... 546/146; 546/147; 546/116; 546/97
[58] Field of Search .................................... 546/116, 146, 546/147, 97

[56] References Cited

U.S. PATENT DOCUMENTS

| 5,157,041 | 10/1992 | Handa et al. | 514/314 |
| 5,196,438 | 3/1993 | Martin et al. | 514/311 |
| 5,256,783 | 10/1993 | Gokhal et al. | 546/146 |
| 5,380,849 | 1/1995 | Houpis et al. | 546/146 |

FOREIGN PATENT DOCUMENTS

| 0346847A2 | 12/1989 | European Pat. Off. | 514/314 |
| 0432695A2 | 6/1991 | European Pat. Off. | 514/311 |
| 0533000A1 | 3/1993 | European Pat. Off. | 514/311 |
| WO93/01174 | 1/1993 | WIPO | 514/314 |

OTHER PUBLICATIONS

E. C. Weir, et al., *Tricyclic Hydantoins and Thiohydantoins of Phenylalanine*, Chimika Chronika, New Series, vol. 18, No. 1, pp. 3–17 (Mar. 1989).

*Primary Examiner*—James H. Reamer
*Attorney, Agent, or Firm*—Marshall, O'Toole, Gerstein, Murray & Borun

[57] ABSTRACT

Methods for preparing (S)-N-tert-butyl-1,2,3,4-tetrahydro-3-isoquinoline-carboxamide ("tic-c"), and converting tic-c to (S)-decahydroisoquinoline-3-carboxylic acid t-butylamide ("tic-d") are disclosed. The initial step in the formation of tic-c involves the phosgenation of a substituted tetrahydroisoquinoline to form an N-carboxy anhydride. Tic-d is used as an intermediate in the synthesis of known compounds having pharmaceutical activity.

16 Claims, No Drawings

PREPARATION OF (S)-DECAHYDROISOQUINOLINE-3-CARBOXYLIC ACID T-BUTYLAMIDE

BACKGROUND OF THE INVENTION

The present invention relates to methods for preparing (S)-N-tert-butyl-1,2,3,4-tetrahydro-3-isoquinoline-carboxamide ("tic-c"), and (S)-decahydroisoquinoline-3-carboxylic acid t-butylamide ("tic-d"), key intermediates in the synthesis of known compounds having pharmaceutical activity. (Tic-d is also referred to as (S)-decahydroisoquinoline-3-carboxylic acid-tert-butylamide in the prior art).

Martin et al, U.S. Pat. No. 5,196,438, describes certain amino acid derivatives which inhibit proteases of viral origin, and which can be used in the treatment of viral infections caused by HIV and other retroviruses. The compounds disclosed by Martin et al have the structural formula:

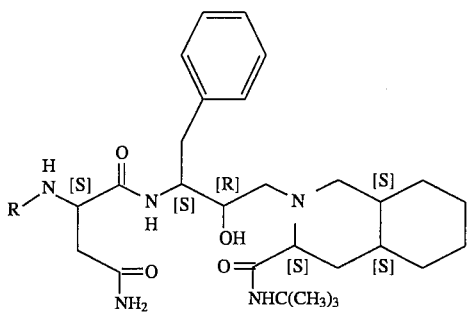

Martin et al have demonstrated that these compounds have in vitro antiviral activity.

Martin et al's synthesis of the above amino acid derivatives involves a step wherein a compound having the formula

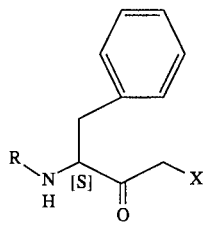

where R' is an amino-protecting group and X is chloride or bromide, is reacted with tic-d:

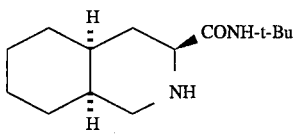

A process for synthesizing tic-d from phenethylamine derivatives is described in EPO Application 0 533 000 A1 (Gokhale et al, published Mar. 24, 1993). The phenethylamine derivatives which are used in the Gokhale et al synthesis can be formed by reacting N-benzyloxycarbonyl-L-phenylalanine with N-ethyl morpholine and isobutyl chloroformate. The resultant phenethylamine derivative has the general formula:

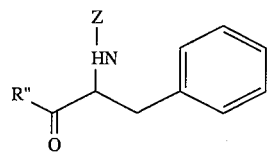

wherein Z is benzyloxycarbonyl and R" can be lower alkylamino. When the forgoing phenethylamine derivative is reacted with formaldehyde or dimethoxymethane in the presence of sulfuric acid in acetic acid, an isoquinoline compound is formed:

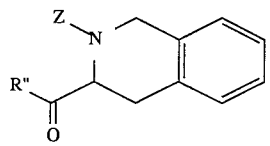

Gokhale et al show that this compound can be transformed to a 1,2,3,4-tetrahydro-2-isoquinoline derivative having the general formula:

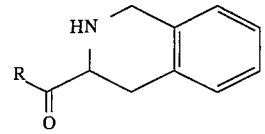

wherein R can be tert-butyl amino. When R is so defined, the compound is systematically named, (S)-N-tert-butyl-1,2,3,4-tetrahydro-3-isoquinoline carboxamide ("tic-c"). Gokhale et al state that tic-c, in turn, can be hydrogenated to tic-d, which can be used in the manufacture of protease inhibitors.

A synthesis of the hydrochloride salt of tic-c is reported in E. C. Weir et al, "Tricyclic Hydantoins and Thiohydantoins of Phenylalanine," Ch. Chron., Vol. 18, No. 1, pp. 1–17 (March, 1989). The compound was formed by reacting t-butyl amine with a tri-cyclic N-carboxyanhydride:

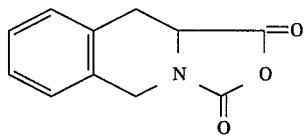

The reaction reported by Weir et al was run in a chloroform solvent; yield of tic-c was reported as 57% (id., Table IV).

The disadvantages of the above processes are: 1) the procedure requires a chlorinated solvent; 2) the yield of desired tic-c product is not good; 3) the process uses $PCl_5$; and 4) the transformation of tic-a to tic-c requires three steps.

SUMMARY OF THE INVENTION

The present invention describes processes for preparing (S)-N-tert-butyl-1,2,3,4-tetrahydro-3-isoquinoline carboxamide ("tic-c"), and for converting this compound to (S)-decahydroisoquinoline-3-carboxylic acid t-butylamide ("tic-d"), an intermediate used in the synthesis of compounds having pharmaceutical activity. The process employs non-chlorinated solvents, and does not isolate a moisture sensitive intermediate, the N-carboxy anhydride of (3S)-1,2,3,4-tetrahydroisoquinoline.

The synthesis can be written as follows:

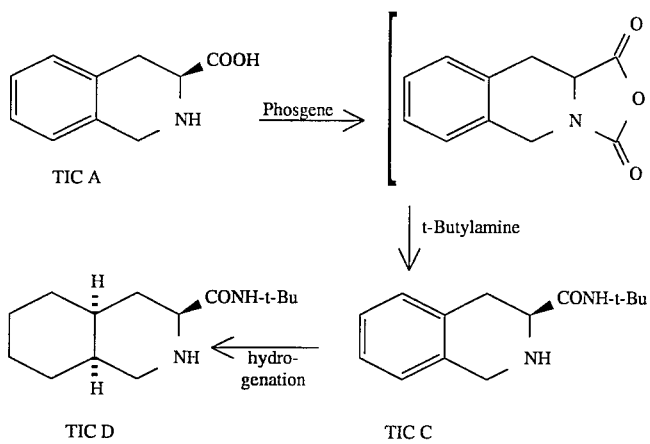

In the method of the present invention, tic-a is first reacted with phosgene to prepare tic-a N-carboxy anhydride (NCA). This intermediate is not isolated, but reacted in situ with tert-butylamine to form tic-c. Tic-c can be extracted from the reaction mixture into aqueous acid to separate it from several impurities, and the resultant acid salt neutralized with base in the presence of an organic solvent (heptane is preferred). In a preferred method, the organic extract is subjected to hydrogenation using a supported rhodium catalyst to convert the tic-c to tic-d. Following catalyst removal by filtration, the tic-d is isolated by concentration, crystallization, filtration and drying. Yields for phosgenation are 75–80%; for hydrogenation and isolation 60–70%; and overall 45–56% for the two steps. One significant advantage of the above procedure is that there is no necessity for isolating the tic-a NCA intermediate.

The preferred starting compound in the method of the present invention is an isoquinoline derivative, (3S)-1,2,3,4-tetrahydroisoquinoline-3-carboxylic acid ("L-tic-a"). This compound can be formed by reacting phenylalanine with formaldehyde in the presence of HCl (the Pictet-Spengler reaction), followed by neutralization of the hydrochloride salt. However, this reaction produces a racemic mixture of L (levorotatory) and D (dextrorotatory) optical isomers [ratio of L:D=70:30 to 90:10]. As noted in copending application Ser. No. 556,249, entitled "An Improved Method for Preparation of Substituted Tetrahydroisoquinolines," filed Nov. 9, 1995, and commonly owned with the present application, the disclosure of which is incorporated herein, the levorotatory isomer of tic-a is a preferred starting material for the synthesis of a number of pharmaceutically active drugs. The procedure described in copending application Ser. No. 556,249 describes the reaction of phenylalanine with formaldehyde in the presence of hydrobromic acid (HBr) to yield substantially optically-pure L-tic-a hydrobromide (>97% ). Because of its ability to produce the desired L-tic-a isomer in high yield, the procedure described in application Ser. No. 556,249 may be a preferred method of forming the tic-a starting material.

The initial step in the process is the formation of a slurry of L-tic-a in an organic solvent. The L-tic-a starting material should have a particle size in the range of about 50–350 mesh; 325 mesh is preferred. Preferred solvents include THF, dioxane, and esters having a boiling point between about 50°–125° C., such as ethyl acetate, isopropyl acetate and butyl acetate. Ethyl acetate is especially preferred. The same chemistry can be used to prepare (R)-N-tert-butyl-1,2,3,4-tetrahydro-3-isoquinoline carboxamide, using D-tic-a as a starting material.

The tic-a slurry is maintained at a temperature in the range of about 0° to 30° C. (15° C. preferred) and phosgene (about 1 to 4 equivalents, 1.3 preferred) is added to form a first reaction mixture. After the phosgene addition step, it is desirable (but not necessary) to maintain the reaction mixture at a temperature between about 20° to 55° C. (35° C. preferred) for a period of time after phosgene addition (½ to 6 hours; 3 hours preferred). Thereafter, the reaction mixture can be heated to reflux for a period of between about 2 to 6 hours (4 hours preferred) to form tic-a NCA. A non-reactive gas (e.g., nitrogen) can be bubbled through the reaction mixture to reduce the amount of residual phosgene (final phosgene and HCl level<0.2 wt %).

The first reaction mixture can then be cooled to an amine-addition temperature in the range of about −20° to 5° C., whereupon 1 to 4 equivalents of tert-butylamine (2.2 equivalents preferred) is added to form a second reaction mixture. Although the reaction between tic-a NCA and t-butyl amine will proceed at low temperature, raising the second reaction mixture to a temperature higher than 5° C. will speed the reaction. Maintaining the second reaction mixture at ambient temperature (approximately 15°–30° C.) for about 1 hour is sufficient to convert the tic-a NCA to tic-c.

In a preferred method for isolating the tic-c product, the reaction mixture is extracted with an aqueous base to remove water-soluble impurities, followed by extraction with an aqueous acid (e.g., sulfuric acid) to produce a water soluble salt (e.g., tic-c sulfate). Neutralization of the acid salt with a base and extraction with an organic solvent (e.g., ethyl acetate or hot heptane) returns the tic-c to the organic phase. Suitable bases include sodium hydroxide, potassium hydroxide, potassium carbonate and sodium carbonate. Evaporation of the organic solvent yields tic-c in 70 to 90% yield.

Tic-c can be converted to tic-d by catalytic hydrogenation under pressure. Two procedures can be employed for this step: hydrogenation of a tic-c acid salt in aqueous media; or, hydrogenation of an organic solution of tic-c. The latter procedure is preferred.

In the aqueous method, crude tic-c formed by the reaction of tic-a NCA with t-butylamine is extracted with an aqueous base to remove water-soluble impurities, followed by the addition of phosphoric acid to form water-soluble tic-c phosphate. The aqueous solution can be hydrogenated using hydrogen gas, by using a catalyst, elevated temperatures (e.g., 80°–100° C., and high pressures (100–350 psi). Suitable hydrogenation catalysts include Rh/C and Rh/Al$_2$O$_3$. The use of 5% Rh/Al$_2$O$_3$ catalyst at 100° C. and a pressure of 350 psi is quite effective. Upon completion of the hydrogenation step, the pH of the solution is adjusted to about 10, extracted with ethyl acetate, and the aqueous layer discarded. Because tic-d is more easily recrystallized from a hydrocarbon solvent, addition of heptane to the ethyl acetate solution, followed by distillation of the lower-boiling ethyl acetate facilitates recovery of solid tic-d.

Tic-c can also be hydrogenated in the organic solvent in which the tic-c synthesis is run (e.g., ethyl acetate), preferably after washing with an aqueous base to remove water-soluble impurities. However hydrogenation in a hydrocarbon solvent, such as heptane, is preferred. Tic-c can be converted to tic-d using hydrogen gas, a Rh/Al$_2$O$_3$ catalyst, and high pressures (100–350 psi) by maintaining the organic solution at a temperature of about 100° C. for a period of 8 to 10 hours. Hot filtration of the resultant solution to remove any catalyst, followed by evaporation to remove the organic solvent, yields tic-d in high yields.

DETAILED DESCRIPTION OF THE INVENTION

The following examples are presented for purposes of illustration and should not be construed as limiting the invention which is delineated in the claim.

EXAMPLE I

N-tert-butyl-1,2,3,4-tetrahydro-isoquinoline-3(s)-carboxamide (TIC-C)

650 lbs. of tic-a is slurried in 1010 gallons of ethyl acetate and 494 lbs. of phosgene (1.3 equivalents) is added at 10°–20° C. over 3 hours. The slurry is held at 30°–±5° C. for 3 hours. Then the slurry is heated to 72°–78° C. for 4 hours. Nitrogen is purged through the solution until the Hcl and phosgene are less than 0.2 wt/wt %. The solution is cooled to −10°–0° C. and 696 lbs. of tert-butylamine (2.6 equivalents) is added. After the addition, the slurry is warmed to 20°–25° C. and held for 1 hour. After the 1 hour hold, 526 gallons of water is added to the slurry and pH adjusted to pH=10–10.5 with potassium hydroxide. The 2 layers are separated with the bottom aqueous layer going to waste. 211 gallons of water is added to the top organic layer and pH adjusted to pH=10–10.5 with potassium hydroxide. The 2 layers are separated with the bottom aqueous layer going to waste. 526 gallons of water is added to the top organic layer and pH adjusted to pH—2.0–2.5 with sulfuric acid. The bottom aqueous layer is collected in drums labeled tic-c sulfate (yield=75–84% ).

EXAMPLE II

N-tert-butyl-decahydro-(4aS,8aS)-isoquinoline-3(s)-carboxamide (TIC-D)

The drums from the above process are pumped into a tank and heptane is added. The 2 phase system is heated to 65°–70° C. and sodium hydroxide is added until pH=10–10.5. The 2 layers are separated with the bottom aqueous layer going to waste. The top organic layer is heated to azeotropically remove the residue water. The solution is hydrogenated using a 15% loading of 5% Rh/Al$_2$O$_3$ at 100° C. under 350 psi for 10–16 hours. The slurry is filtered hot to remove the catalyst. The filtrate is concentrated to 25–33% wt/wt % tic-d and cooled to 10° C. over 8–10 hours. The solids are collected by filtration and washed with heptane to give tic-d as a white solid (yield=62–67%).

Overall yield from tic-a=47–56%.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the process may be varied substantially without departing from the spirit of the invention, and the exclusive use of all modifications which come within the scope of the appended claims is reserved.

We claim:

1. A method of preparing (S)-N-tert-butyl-1,2,3,4-tetrahydro-3-isoquinoline-carboxamide which comprises the following steps:

forming a first reaction mixture in a reaction vessel, said mixture comprising: (3S)-1,2,3,4-tetrahydroisoquinoline-3-carboxylic acid, 1 to 4 equivalents of phosgene, and an organic solvent having a boiling point between about 50° and 125° C.;

heating said first reaction mixture to an elevated temperature in the range of about 50° to 125° C., and maintaining the reaction mixture at said elevated temperature for a period of about 2 to 6 hours to produce an N-carboxy arthydride;

cooling said first reaction mixture to an amine-addition temperature in the range of about −20° to 5° C.;

adding between 1 and 4 equivalents of tert-butyl amine to said reaction vessel to form a second reaction mixture; and maintaining said second reaction mixture at a temperature of greater than 5° C. until said N-carboxy anhydride has been converted to (S)-N-tert-butyl-1,2,3,4-tetrahydro-3-isoquinoline-carboxamide.

2. The method of claim 1 wherein said organic solvent is selected from the group consisting of: tetrahydrofuran, dioxane, ethyl acetate, butyl acetate and isopropyl acetate.

3. The method of claim 1 wherein said organic solvent comprises ethyl acetate.

4. The method of claim 1 wherein said (3S)-1,2,3,4-tetrahydroisoquinoline-3-carboxylic acid has a particle size in the range of about 50 mesh to about 350 mesh.

5. The method of claim 1 wherein said first reaction mixture has an initial temperature in the range of between about 0° C. and 30° C., and said reaction mixture is maintained at a temperature between about 20° C. and about 55° C. for a period of between about ½ hour and 6 hours.

6. The method of claim 1 wherein the level of phosgene in said first reaction mixture is less than about 0.2 wt % at the point of amine addition.

7. The method of claim 1 further including the step of bubbling a non-reactive gas through said first reaction mixture until the amount of phosgene in said first reaction mixture is less than 0.2 wt %.

8. The method of claim 1 wherein said second reaction mixture is maintained at a temperature in the range of about 15° C. to about 30° C. for a period of about one hour.

9. The method of claim 1 further including the steps of purifying said (S)-N-tert-butyl-1,2,3,4-tetrahydro-3-isoquinoline-carboxamide, comprising:

washing said second reaction mixture with an aqueous base;

discarding the resultant aqueous phase; and extracting said second reaction mixture with an aqueous acid to form an aqueous phase containing a water-soluble salt of said carboxamide.

10. The method of claim 9 further including the following steps:

neutralizing said water-soluble salt with a base;

extracting said aqueous phase with an organic solvent to form an organic solution containing (S)-N-tert-butyl-1,2,3,4-tetrahydro-3-isoquinoline-carboxamide.

11. The method of claim 10 wherein said organic solvent is heptane.

12. A method of preparing N-tert-butyl-decahydro-(4aS, 8aS) isoquinoline-3(S)-carboxamide which comprises the following steps, in sequence:

forming a first reaction mixture in a reaction vessel, said mixture comprising: (3S)- 1,2,3,4-tetrahydroisoquinoline-3-carboxylic acid, 1 to 4 equivalents of phosgene, and an organic solvent having a boiling point between about 50° and 125° C.;

heating said first reaction mixture to an elevated temperature in the range of about 50° to 125° C., and maintaining the reaction mixture at said elevated temperature for a period of about 2 to 6 hours to produce an N-carboxy anhydride;

cooling said first reaction mixture to an amine-addition temperature in the range of about −20° to 5° C.;

adding between 1 and 4 equivalents of tert-butyl amine to said reaction vessel to form a second reaction mixture;

maintaining said second reaction mixture at a temperature of greater than 5° C until said N-carboxy anhydride has been converted to (S)-N-tert-butyl-1,2,3,4-tetrahydro-3-isoquinoline-carboxamide;

washing said second reaction mixture with an aqueous base and discarding the resultant aqueous phase, to produce an organic solution which contains purified (S)-N-tert-butyl-1,2,3,4-tetrahydro-3-isoquinoline-carboxamide; and hydrogenating said purified carboxamide, under pressure, in the presence of a catalyst to form N-tert-butyl-decahydro-(4aS,8aS)isoquinoline-3(S)-carboxamide.

13. The method of claim 12 which further comprises steps, subsequent to said washing step, as follows:

extracting said purified carboxamide with an aqueous acid to form an aqueous phase which contains a water-soluble salt of said carboxamide, and discarding the organic phase; and neutralizing said water-soluble salt with a base while simultaneously extracting said aqueous phase with a hydrocarbon solvent.

14. The method of claim 13 wherein said hydrocarbon solvent comprises heptane.

15. The method of claim 12 wherein said catalyst comprises $Rh/Al_2O_3$.

16. A method of preparing (R)-N-tert-butyl-1,2,3,4-tetrahydro-3-isoquinoline-carboxamide which comprises the following steps:

forming a first reaction mixture in a reaction vessel, said mixture comprising: (3R)-1,2,3,4-tetrahydroisoquinoline-3-carboxylic acid, 1 to 4 equivalents of phosgene, and an organic solvent having a boiling point between about 50° and 125° C.;

heating said first reaction mixture to an elevated temperature in the range of about 50° to 125° C., and maintaining the reaction mixture at said elevated temperature for a period of about 2 to 6 hours to produce an N-carboxy anhydride;

cooling said first reaction mixture to an amine-addition temperature in the range of about −20° to 5° C.;

adding between 1 and 4 equivalents of tert-butyl amine to said reaction vessel to form a second reaction mixture; and maintaining said second reaction mixture at a temperature of greater than 5° C. until said N-carboxy anhydride has been converted to (R)-N-tert-butyl-1,2,3,4-tetrahydro-3-isoquinoline-carboxamide.

* * * * *

UNITED STATES PATENT AND TRADEMARK OFFICE
CERTIFICATE OF CORRECTION

PATENT NO.   :  5,587,481

DATED        :  December 24, 1996

INVENTORS    :  Allen et al.

It is certified that error appears in the above-identified patent and that said Letters Patent is hereby corrected as shown below:

Column 5, line 35 replace "30°-±5°C." with --30 ± 5°C--

Column 6, line 26 replace "arthydride" with --anhydride--

Signed and Sealed this

Twenty-second Day of July, 1997

Attest:

BRUCE LEHMAN

Attesting Officer

Commissioner of Patents and Trademarks